United States Patent [19]

Huang et al.

[11] Patent Number: 5,410,676
[45] Date of Patent: Apr. 25, 1995

[54] INFORMATION SYSTEM USING DESIGNATING AREAS FOR RETRIEVING/CONVERTING DATA AND DIRECTORIES OF DIFFERENT FORMATS STORING IN OPTICAL AND MAGNETIC STORAGE

[75] Inventors: Han K. Huang, Agoura Hills; Craig A. Morioka, Los Angeles; Osman Ratib, Pacific Palisades; Paul N. S. Cho, Culver City; Bruce K. T. Ho, Los Angeles, all of Calif.; Takeo Sonobe; Toru Shinagawa, both of Toride, Japan

[73] Assignee: The Regents of the University of California, Alameda, Calif.

[21] Appl. No.: 967,558

[22] Filed: Oct. 27, 1992

Related U.S. Application Data

[63] Continuation of Ser. No. 401,146, Aug. 31, 1989, abandoned.

[51] Int. Cl.$^6$ .......................... G06F 15/40; G06F 7/22
[52] U.S. Cl. ................................ 395/500; 364/260.81;
       364/952.31; 364/952.4; 364/963; 382/64;
       382/65; 369/13
[58] Field of Search .................. 369/13, 14, 15, 275.1,
       369/275.2, 275.3; 382/64, 65; 395/500

[56] References Cited

U.S. PATENT DOCUMENTS

| | | | |
|---|---|---|---|
| 3,886,325 | 5/1975 | Dorr et al. | 364/200 |
| 4,141,005 | 2/1979 | Bonner et al. | 340/347 DD |
| 4,281,315 | 7/1981 | Bauer et al. | 340/147 R |
| 4,419,750 | 12/1983 | Howe | 369/111 |
| 4,433,377 | 2/1984 | Eustis et al. | 364/200 |
| 4,485,439 | 11/1984 | Rothstein | 364/200 |
| 4,559,614 | 12/1985 | Peek et al. | 364/900 |
| 4,661,988 | 4/1987 | Shimizu | 382/65 |
| 4,760,526 | 7/1988 | Takeda et al. | |
| 4,791,558 | 12/1988 | Chaitin et al. | |
| 4,802,152 | 1/1989 | Markvourt et al. | 369/32 |
| 4,833,471 | 5/1989 | Tokuume et al. | 341/67 |
| 4,866,601 | 9/1989 | DuLac et al. | 364/200 |
| 4,896,289 | 1/1990 | Svinicki et al. | 364/900 |
| 4,918,661 | 4/1990 | Yamauchi | 369/30 |
| 4,956,806 | 9/1990 | Crowe et al. | 364/900 |
| 5,040,232 | 8/1991 | Kanno | 382/44 |
| 5,053,945 | 10/1991 | Whisler | 395/600 |
| 5,070,474 | 12/1991 | Tuma et al. | 395/500 |

FOREIGN PATENT DOCUMENTS

| | | |
|---|---|---|
| 0165382 | 12/1985 | European Pat. Off. |
| 0372703 | 6/1990 | European Pat. Off. |
| 3823252A1 | 1/1989 | Germany |

OTHER PUBLICATIONS

R. H. van Bilderbeek and L. A. Valkenburgh, "Device-Independent Conversion Program", IBM Technical Disclosure Bulletin, 15(2):683, Jul. 1972.

Mankovich et al., *RSNA Annual Meeting–UCLA* (1986), "Operational Radiologic Image Archive on Digital Optical Disks".

Huang et al., *Medical Imaging Technology* 4:2 (1986) "PACS at UCLA I-A Status Report".

*Primary Examiner*—Parshotam S. Lall
*Assistant Examiner*—Krisna Lim
*Attorney, Agent, or Firm*—Merchant & Gould

[57] ABSTRACT

Data and directories are separated and stored on separate parts of an optical disk. Data and directories are written from magnetic disk storage in a first specific format that is determined by a particular operating system used by an information processor. Directories are on the inner tracks and data are on the outer tracks, in a second format on the optical disk. A medical information processing system is provided with an external magnetic disk storage and the optical disk.

26 Claims, 7 Drawing Sheets

FIG. 12

INFORMATION SYSTEM USING DESIGNATING AREAS FOR RETRIEVING/CONVERTING DATA AND DIRECTORIES OF DIFFERENT FORMATS STORING IN OPTICAL AND MAGNETIC STORAGE

This is a continuation of application Ser. No. 0 7/401,146 filed on Aug. 31, 1989, now abandoned.

BACKGROUND

This invention relates to an information processing system. More particularly the invention is directed to an information storage and processing system that is effectively configured to ensure compatibility of removable stored media among different systems.

Apparatus of this type includes optical disk filing systems and word processors which store information in different proprietary formats. These different formats are inconvenient and have hindered the spread of such systems, because removable stored media from one system are not compatible with other systems. Accordingly, information stored on one system has not been usable on another system.

More particularly the invention concerns 5.25-inch and 3.5-inch optical disks (OD) . International Standards Organization which conform to "ISO" SC23. The storage capacity of a 3.5-inch optical disk is about 100 megabytes (MB), and that of a 5.25-inch optical disk is about 600 MB. The storage capacity of such discs is much greater than the capacity of equivalent physical size other storage media such as magnetic disks.

Recently there have been studies for using such media to store personal medical history data. In a radiological application, a single conventional x-ray with a resolution of 2,048 by 2,048 pixels by 10 bits requires 5 MB of storage space. An ultrasound sonogram requires about 0.25 MB, and a nuclear magnetic resonance (NMR) image requires about 0.07 MB.

Due to the enormity of the radiological data needed to be stored, it has been a developing practice at least in one hospital, namely, the University of California Los Angels "UCLA" Medical School in Los Angeles, Calif., to store this data on mainframe optical discs. These are physically about 12" to 14" discs and are permanently housed in mainframe computer storage facilities as part of a digitally based picture archiving and communicating system (PACS). This system replaces conventional x-ray films operating systems. A problem with PACS, however, is the difficulty of data retrieval. PACS is structured on a "first-in-first stored" system, and hence when particular data is required about a particular patient, a long lead time is necessary to assemble all that data for display.

By recording a patient's diagnostic data on an optical disk file, it is possible to maintain an up-to-date record of each patient's entire medical history. This would be useful for diagnostic purposes. To date this has not been possible with existing storage media.

Computer systems have made progress in recent years, and a variety of systems are now available. For instance, personal computers commonly used in hospitals and physician offices are currently based essentially on either an IBM PC/AT (Trademark), Macintosh (Trademark), or SUN (Trademark) information processing systems. The term IBM PC/AT processing system includes different clone systems. Such operating systems however are basically incompatible and this limits the ability to process information and transfer data from one system to another.

It is desirable in carrying out a diagnosis, that stored personal medical information be usable on different computer systems within the same hospital or at other hospitals. It should also be possible to record and store data obtained in the radiologic diagnosis on the storage media operable with the different computer systems.

With conventional information processing systems, storage media and computer systems this has not yet been achieved.

SUMMARY

An object of the invention is to provide an information processing system which is highly usable. The system seeks to solve the incompatibility problems between different conventional computer, processing and storage systems.

Another object of the invention is to provide a compatible system that can be used with optical disks containing data stored in a compatible format that differs from the storage format used by the operating system of a computer system concerned. It is an object to provide a system which employs essentially a digital or binary format for data processing, storage and display which is essentially compatible with multiple computer operating systems.

Compatibility between different systems can be achieved by making the information stored on removable media the same, or partly the same, and providing each system with a translation capability.

According to the invention an information processing system comprises an information processor for processing information, the processor having a specific operating system. There is an external storage for connection to the information processor, the external storage having data and directories written and read in a first format based on the specific operating system.

A format converter for connection to the external storage and the information processor converts data and directories in the first format from the external storage to data and directories in a second format. The format converter includes designation means for designating different areas for storing the data and the directories in the second format. The format converter also converts data and directories from the second format to the first format.

An optical disk drive connected to the format converter permits storing of the data and the directories in the second format on an optical disk.

The designation means includes sequential storage means whereby the directories are recorded sequentially on the optical disk starting from an inner track and the data are recorded sequentially on the optical disk starting from an outer track. There is means for dividing data read from the external storage into an optical disk sector portion.

Also respective designation means designates that the data and the directories read from the optical disk by the optical disk drive are each stored in a continuous form in one area of the external storage. Different format data and directories separately read from the optical disk by the optical disk drive are combined and converted to data in the first format.

Further according to the invention, there is a method for processing and storing data in an information processing system provided with an information processor, a magnetic disk system for connection to the information processor and for storing data designated by the information processor, and an optical disk drive for storing data designated by the information processor. Data and directories in a first format based on a specific operating system of the information processor are combined, and the combined data and directories are stored on the magnetic disk system.

The data and directories stored on the magnetic disk system are separated in the first format, and the data in the first format is divided into sector units used by the optical disk in the optical disk drive. The divided data is stored on the optical disk and directories containing file names is stored onto the optical disk on which data divided into sector units have been stored.

In data storing, the data are written sequentially onto the optical disk in sector length units, starting from an outer track. In directory storing, the directories are written sequentially starting from an inner track.

With the invention, medical information can be stored on a removable and portable optical disk. This disk can then be inputted into different computer systems, which would otherwise have normally have incompatible operating systems. The information can then be read out into the different computer systems for information processing. Moreover, new information and data can be written onto the disk by the different computer operating systems.

The invention is further described with reference to the accompanying drawings and an embodiment using optical disks as a removable storage media.

DESCRIPTION

Figure 1:
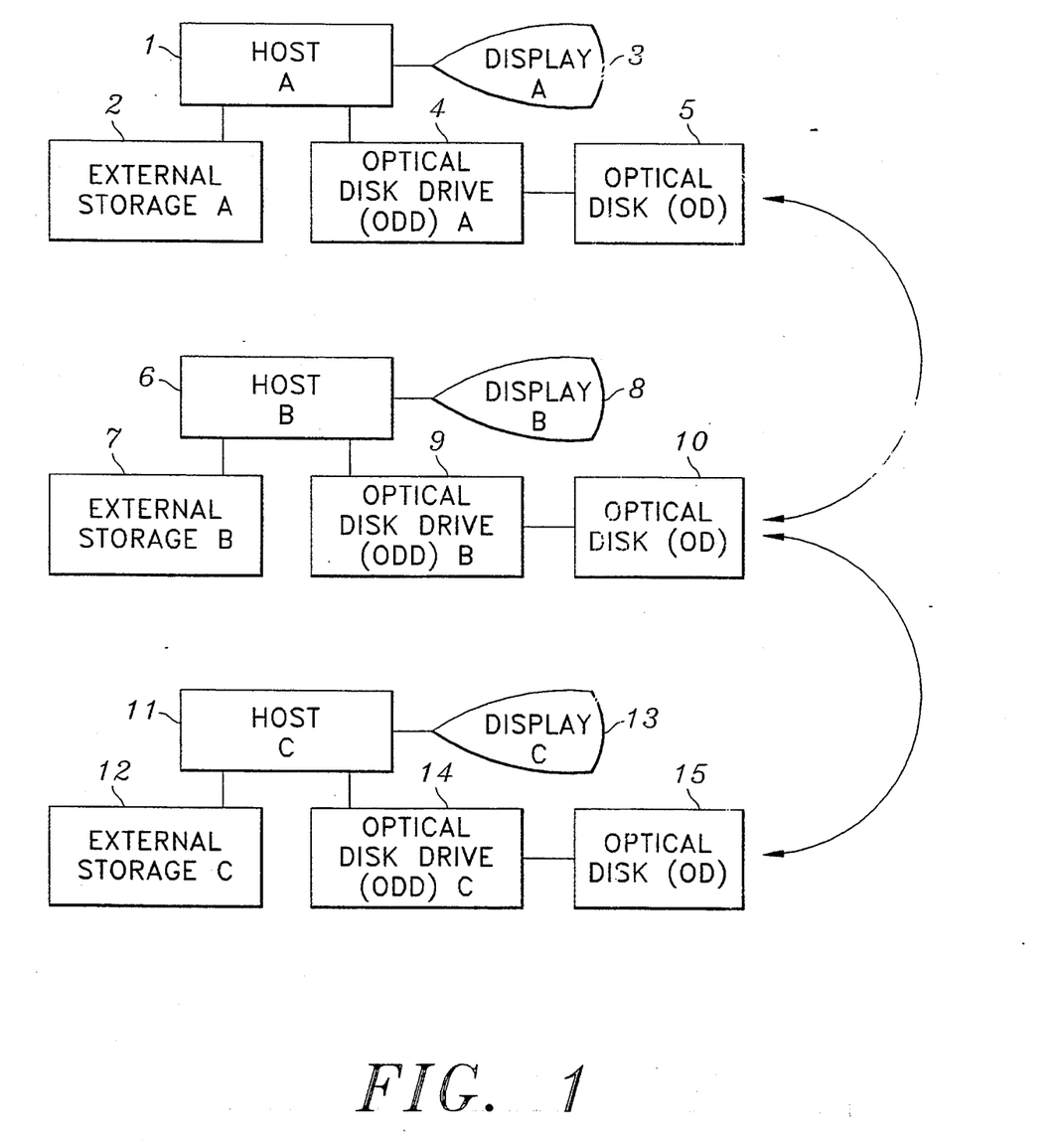
FIG. 1 illustrates a computer system configuration of an embodiment of three different computer systems showing the intercompatibility through the optical disks.

With reference to FIG. 1, a system configuration comprises a host computer system 1. The computer usually is at least a 16-bit model. There is also a first storage, namely, an external storage 2 such as a magnetic disk, and a display 3 capable of a resolution of at least 1,024 by 1,024 pixels by 8 bits. An optical disk drive 4 for 5.25-inch or 3.5-inch disks is connected with the computer system 1. An optical disk 5, namely, a second storage, which has stored data is supplied for the disk drive 4.

In FIG. 1, the system configuration is illustrated for a computer system A, designated by numeral 1, computer system B designated by numeral 6, and computer system C designated by numeral 11. Each of these computer systems, A, B and C, could respectively be different. For instance, an IBM PC/AT (Trademark) Macintosh (Trademark) or SUN (Trademark) system. The operating systems are respectively different. As indicated, each has its own optical disks 5, 10 and 15 respectively. The arrowed line interconnecting the three optical disks 5, 10, 15 designations indicates that the disks 5, 10 and 15 is intercompatible with any of the systems.

Figure 2:
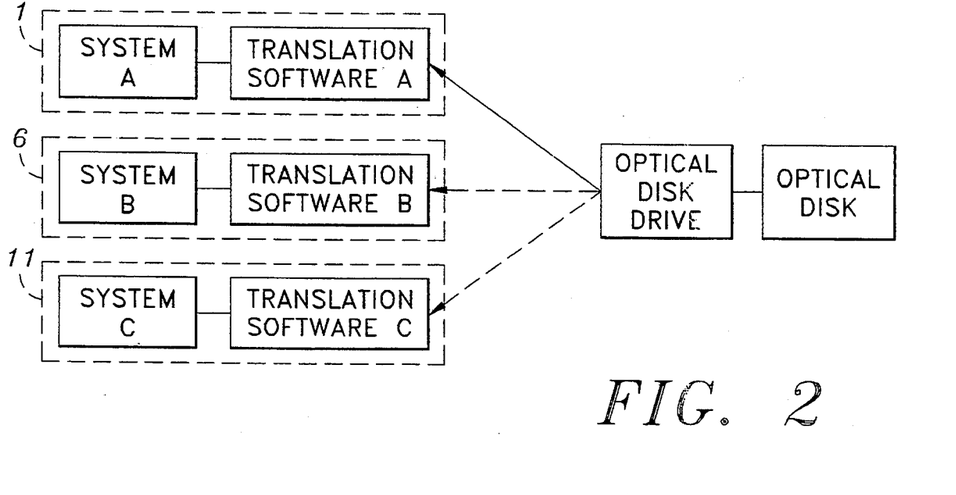
FIG. 2 illustrates an embodiment of the filing format and operation of three different computer systems.

FIG. 2 illustrates a specific optical disk filing format and computer system operation. This format is the same on all computer systems A, B and C. An optical disk drive is used to perform optical disk read/write operations when connected to one or another of the computer systems A, B or C. Since each system A, B and C handles files in a different way, additional translation software A, B or C respectively is required to convert the files for each respective computer system, A, B or C. Thus three different translation software programs A, B and C would be provided to render the optical disk information accessible to the respective computer systems 1, 6 and 11. This permits for the optical disk data to be read, processed and stored in the external storage 2, 7 and 12, respectively, of each computer system 1, 6 and 11, and the optical disk drives 4, 9 and 14 of those systems. Specifically, the data can be displayed on respective screens 3, 8 and 13 of the respective computer systems. This is further illustrated in FIG. 3.

Figure 3:
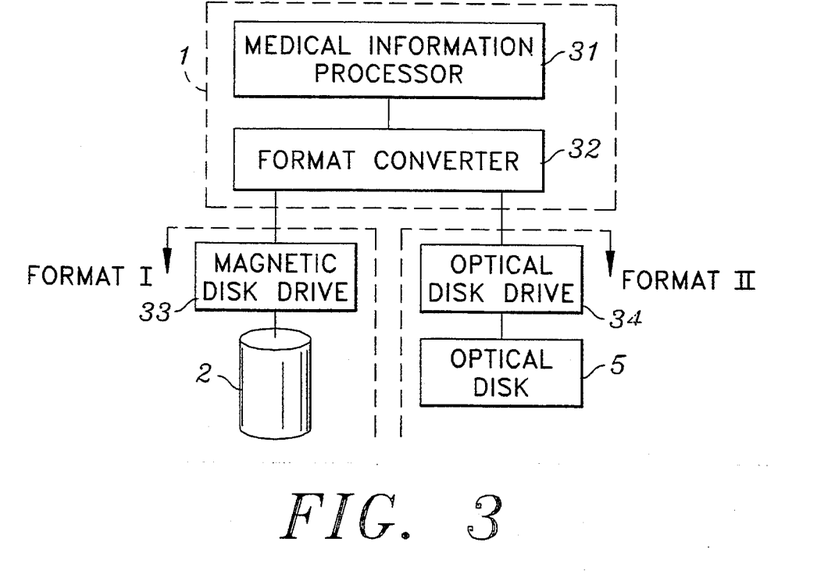
FIG. 3 is an explanatory drawing showing an embodiment of the software configuration of an exemplary computer system.

FIG. 3 shows an example of the software configuration of a medical information processing system. A medical information processor section 31 converts and outputs data read in from the optical disk 5 or data input from an external source 2. Programs and data for the computer system 1 are usually stored in the external floppy magnetic disk storage 2 in the first format used by the operating system concerned. This format is termed Format I. A magnetic disk drive 33 is equipped with the ability to write to the external storage 2 data converted to Format I by a format converter 32, and to read out data from the external storage 2.

Each computer system 1 is equipped with a format converter 32 for data conversion between a first format in which the data is stored on a magnetic disk external storage 2 and to a second format for stored on the optical disk 5. An optical disk drive 34 is provided with the capabilities of reading and writing data. Medical image and other such data are stored on the optical disk 5 in a second format. This format is termed Format II. When the data stored on the optical disk 5 are to be read out, displayed or otherwise processed by the medical information processing section 31, data that have been read out in Format II are converted by the format converter 32. The converted data is sent to the medical information processing section 31 from the format converter 32.

Data conversion between the external storage 2 and the optical disk 5 is also possible. In this case the format converter 32 converts each such format I or II to the other format II or I respectively. Thus, when using a format I that differs from Format II of the operating system data stored on the external storage 2 and the optical disk 5 can be made uniform by conversion between Formats I and II without depending on the operating system. Compatibility is thus provided among the plurality of different computer systems 1, 6 and 11.

Image data in files are stored on an external storage 2 for the computer system 1 host computer A in a Format I based on the particular used operating system used.

Figure 4:
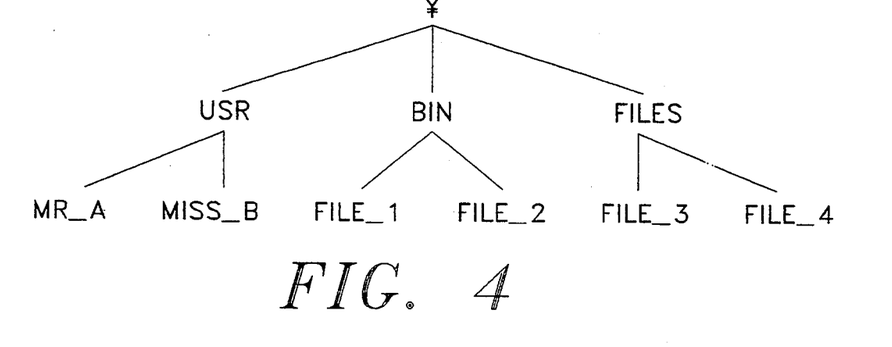
FIGS. 4 and 5 illustrate the directory structure of the external storage for an exemplary computer system.
Figure 5:
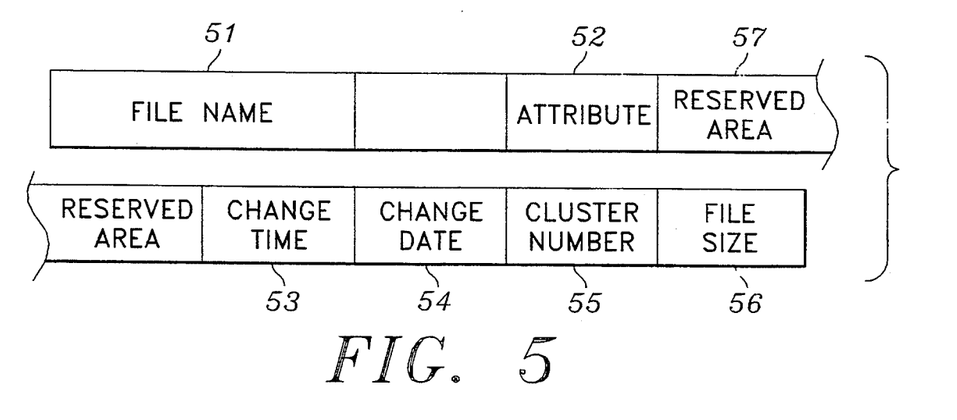

FIGS. 4 and 5 illustrate the directory structure of an external storage 2, showing the location and type of the image data.

As indicated in FIG. 4, and for the purposes of the description, it is assumed that the image data is in FILE_3. Image file FILE_3 can be accessed on the basis of the directory information. In FIG. 5 the directory information is illustrated. This includes a file name 51 given to each file, attribute 52 indicating the type of file, and the time 53 and date 54 the file was recorded on the disk 5. The header cluster number indicates the first data set of the file, and the file size 56.

Figure 6:
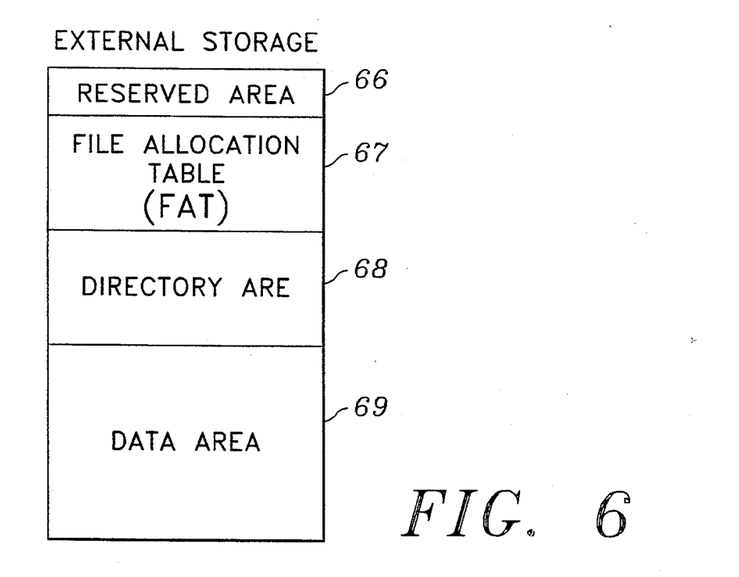
FIG. 6 shows the memory map of the external storage.

The external storage 2 contains four areas shown in the memory map of FIG. 6. There is a reserved area 66, a file allocation table (FAT) area 67, a directory area 68 and a data area 69. The data area 69 is divided into sectors, which form the access units and clusters. Each of these consists of a plurality of sectors. External access is performed on a cluster basis. The FAT area 67 has locations corresponding to each of the clusters in the data area. This includes the number of the cluster containing the next portion of the data in the file.

Figure 7:
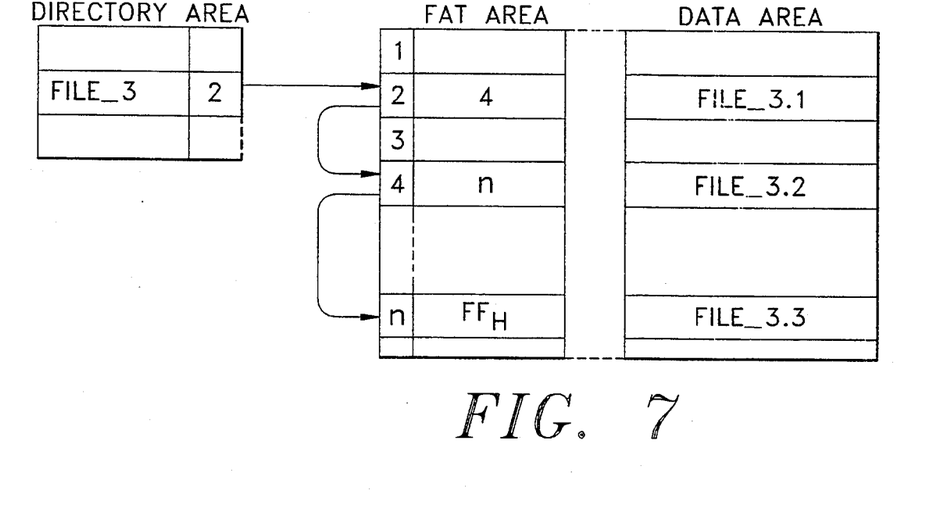
FIG. 7 is an explanatory drawing illustrating a search for cluster numbers in a file allocation table (FAT).

Image file FILE_3 is stored in Format II in the external storage 2. The data are not necessarily stored in contiguous locations but may instead be divided up as shown in FIG. 7. The sequence for reading out FILE_3 from the external storage 2 of the computer system 1 is described with reference to FIG. 7.

To read out FILE_3, the computer system 1 host computer A first accesses the directory area to locate the directory information relating to FILE_3. The data in cluster 2 is obtained from the header cluster number information. Following this, cluster 4 is read out from the cluster 2 area of the FAT. Cluster 4 containing the next portion of the data is then accessed. This read operation is repeated to acquire the data in a continuous flow until the cluster in the FAT area containing an end-of-file marker $FF_H$ is reached.

Figure 8:
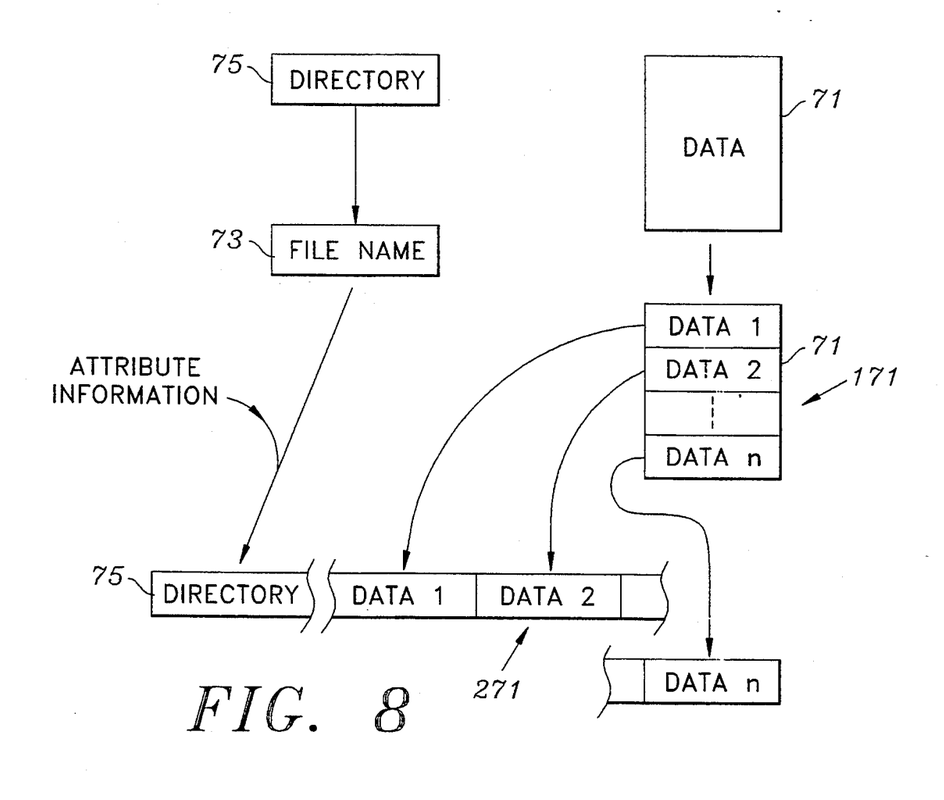
FIGS. 8, 8a, 8B and 9 illustrate the format conversion of data being transferred between an optical disk and a magnetic disk of the external storage.

FIG. 8 illustrates the method of format converting FILE_3 data and directory information read out from the magnetic disk of the external storage 2. Image file data and directory information are stored in the external storage 2, as shown in FIG. 7. The magnetic disk drive 33 reads out image data from the external storage 2 and writes it into the memory of the computer system 1 host computer A.

The format converter program in computer A interprets the attribute information from the first file 73. These attributes which are added would indicate whether the file is an image from a CT scan, MR scan or an X-ray scan. This is added to the directory 75. File name 73 would be indicative of FILE_3 or FILE_4, and directory 75 would be indicative of DIR_3 or DIR_4. The format converter then writes only the data onto the memory of the system computer A. It repeats the similar procedures for the second file, for instance, FILE_4, and writes the DATA 2 onto the immediately adjacent memory which holds the data, DATA 2 from the last file (FILE_3) and so forth. As a result a contiguous block of memory 171 in computer A contains all image data 71. This block 171 of image data 71 is transferred and designated by the format converter program to the optical disk as multiple files or consecutive DATA 1, DATA 2, namely section 271.

At the same time, a 1,024 byte file directory block for instance DIR_3, DIR_4, is generated for each file, for instance, FILE_3, FILE_4. These file directory blocks are written on the optical disk 5 as the optical disk directories. Both the information contained in the file directory blocks and the image data files, for instance, FILE_3, and FILE_4, is the direct result from the format converter program. The format of the file directory block is set out below.

Figure 8A:
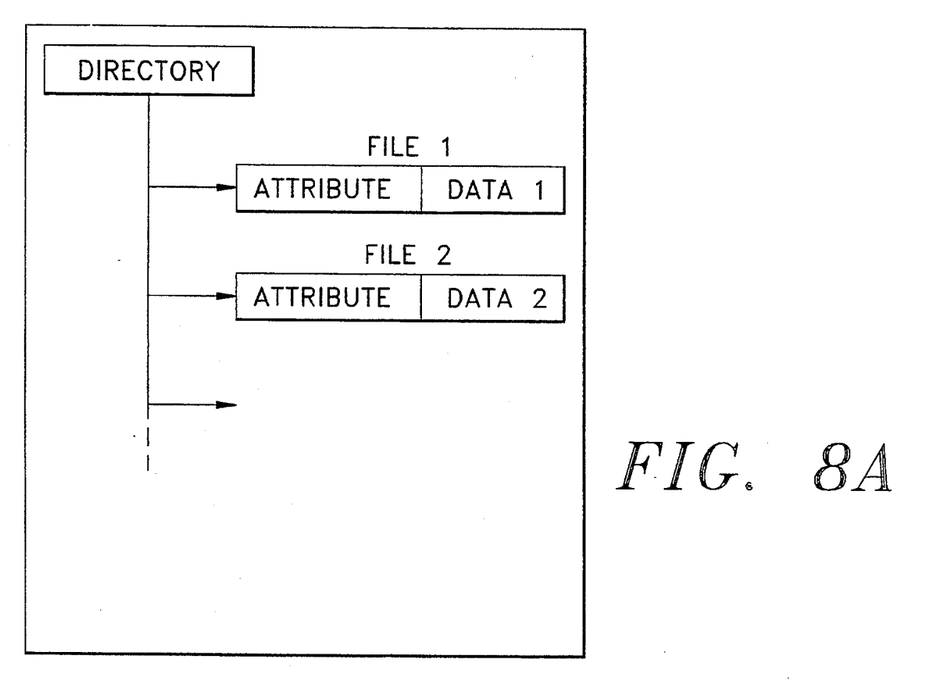
Figure 8B:
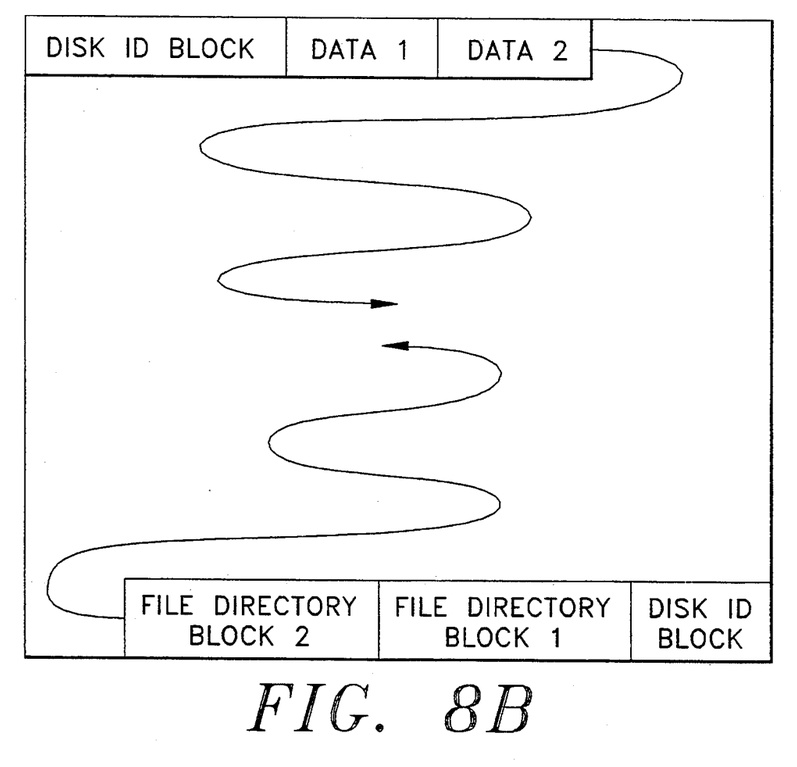

The format converter method of separating the files from the magnetic disk 2 to the optical disk 5 is given in FIG. 8a and FIG. 8B.

Initially on a magnetic disk 2 the file structure is stored in a non-consecutive fashion with a directory pointing to the proper locations of individual files stored with gaps between them. The format converter transfers this data to the optical disk 5 for storage in a consecutive manner with the files and directories separated and each respectively consecutive. When transferring this data back from the optical disk 5 to the magnetic disk the data is consecutively stored in a manner similar to the optical disk storage. This provides for efficient retrieval of information, such as radiological medical images, from a personal computer storage.

In addition an optical disk 5 ID block is automatically generated when a new optical disk is created.

Disk ID and File Directory Blocks

Disk ID Block:

The disk ID is written at the time of disk initialization. The ID block is written at the very first sector (LBN=0) and also at the very last sector (LBN=MAX). The redundancy is for security.

Signature,: 8 char
Version #: 2 char
Protection code: 16 char (optional password)
Disk Name: 32 char
Initialization Date: 11 char (dd-mmm-yyyy)
Comment: 512 char
(*current signature: UCLAPACS version #01)

File Directory Block:

The file directory block is written upon successful archive of a file.

File Name,: 32 char
Address: long int
File Size: long int (specified in bytes)
Archival Date: 11 char (dd-mmm-yyyy)
Creation Date*: 11 char (dd-mmm-yyyy)
File Type,: int (0=IMAGE, 1=ASCII, 2=PICT, etc)
Study Type,: 32 char (for images only)
(*=user supplied parameters)

FIG. 8 shows the directory information of FIG. 4. This includes information in an operating system dependent format.

Figure 9:
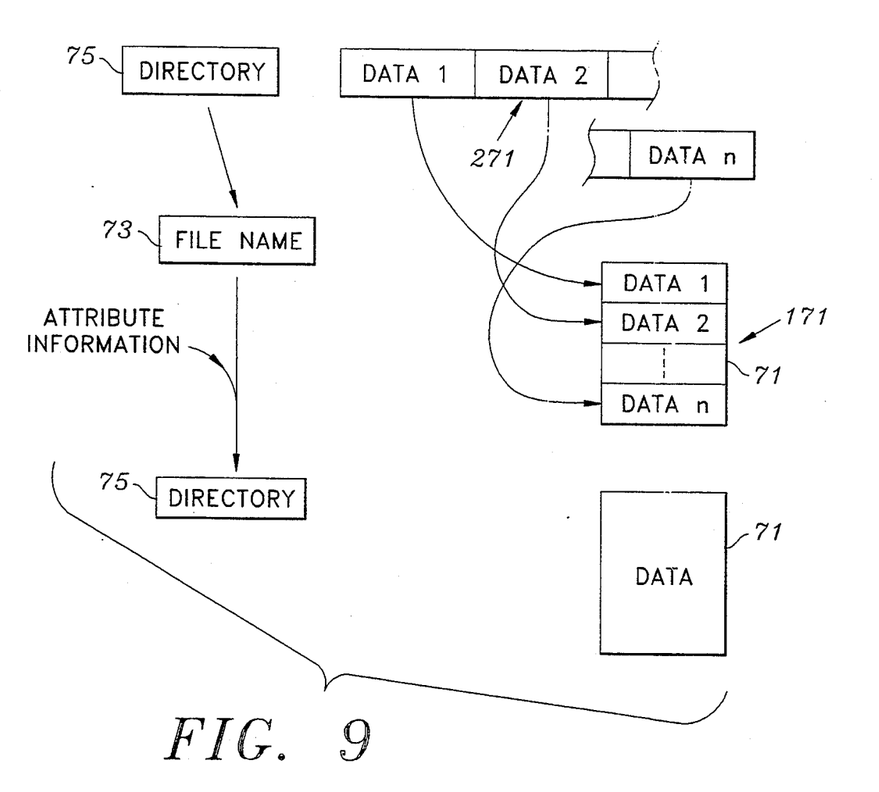

To retrieve image data from the optical disk 5, the following steps as illustrated in FIG. 9 are followed:

1. Read all file Directory Blocks 75, for instance, DIR_3, DIR_4, from the optical disk 5.
2. Present all the Directories to the user through computer A.
3. User selects file names, for instance, FILE_3, FILE_4, from the Directories.
4. Each 1,024 byte file directory 75 helps the format converter program to locate the image data 71 from the optical disk 5.
5. The format converter program assigns new proper attribute information and copies the new attributes with the image data 71 onto the magnetic disk 2 and forms a new image file 171.

Image data read out from the external storage 2 and stored in the computer system 1 are in a format in which they can be displayed on the display 3 by means of the display functions of the computer system 1. The format converter 32 retrieves file name 73 from the directory information that has been read into the computer system 1.

Figure 10:
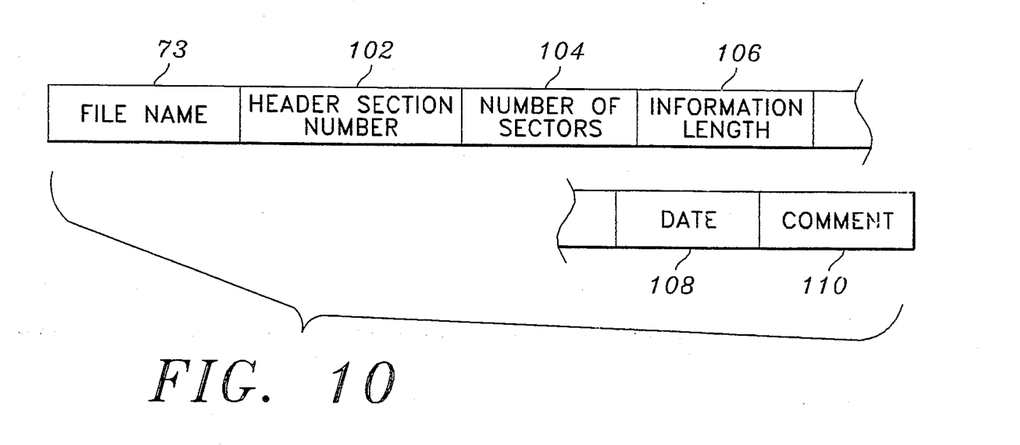
FIG. 10 is an illustration of an optical disk data directory.
Figure 11:
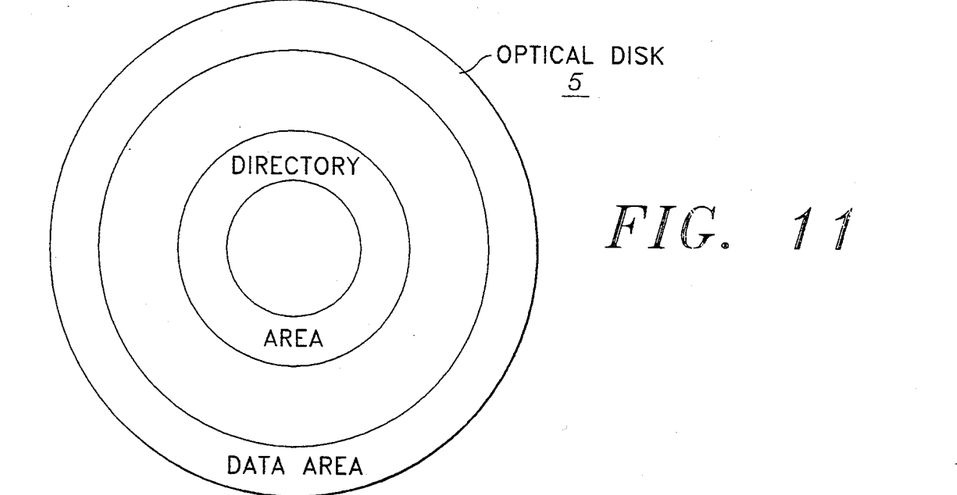
FIGS. 11 and 12 illustrate the data and directory storage areas on an optical disk.

As indicated in FIG. 10, which is the optical disk directory, different items are added to the file name 73. Comment 110 is then added to the header sector number 102, number of sectors 104, information length 106 and date 108 to generate the directory information. This is recorded in the directory area of the optical disk as shown in FIG. 11. Details of this are described below.

The image files are stored on the optical disk 5 as separate data and directory entries. The image data are stored at a location where the images can be recorded as contiguous blocks of data. Directory information is stored at a separate location from the data. Due to this, the format converter 32 shown in FIG. 3 uses the image data length information to calculate the number of sectors required to store the image data on the optical disk 5. Storage areas on the optical disk 5 which are not in use are then located and the header sector numbers of the areas to which image data and directory information can be written are calculated.

Date information is obtained from a real-time clock, for example, provided in the computer system 1. If necessary, a comment can be inputted into the computer system 1 via a keyboard, for example, and will be added to the directory information. The format converter 32 thus generates the directory information stored on the optical disk 5. Image data stored on the optical disk 5 are sequentially read out from the system memory of the computer system 1 and are divided into sector lengths, for example, 1,024 bytes. These form the units in which data on the optical disk 5 are accessed. In this way, an image file that has undergone format conversion is transferred by the optical disk drive 34 into areas designated by the format converter 32.

FIG. 9 illustrates the operation of the image data stored on the optical disk 5 in format I being read out by the computer system 1 and converted to format II by the format converter 32.

As shown in FIG. 11, a data area to store the data and a directory area to store the directory corresponding to the data are established on the optical disk 5. When the image data stored on the optical disk 5 are read out, first the directory information corresponding to the designated file name is read from the directory area of the optical disk 5. The header sector number of the data of the designated file is acquired together with the size, and the data are read out.

Image data read out from the optical disk 5 by the computer system 1 are, as shown in FIG. 9, stored contiguously on the optical disk 5. The format converter 32 extracts the file name from the directory information obtained from the optical disk 5. The conversion date and time, cluster number, size and the required attributes for format II are added. Directory information for the new format II is then generated. Following this the image data are written to the external storage 2 by the method shown in FIG. 7.

A format is established that is independent of the storage format, for instance, Format II of the operating system used by the computer system 1. The first and second formats, namely, Format I and Format II, can be converted each way by the format converter 32. In the past, when storage having a different format was used, software was employed to perform a one-to-one conversion. As this merely preserved compatibility among the same specific formats, the range of application was limited.

By providing each computer system 1, 6 and 11 with a format converter 32 written in computer program language of System 1, 6, and 11 respectively, compatibility is maintained over a broader range. In addition, the format converter 32 incorporated by each computer system 1, 6 and 11 is provided with a conversion function for conversion between the operating system-based format of only each respective computer system 1, 6 and 11 and the specific format of the optical disk format 5, 10 and 15. This facilitates the generation process and makes it possible to adapt to the addition of new computer systems 1, 6 and 11.

Figure 12:
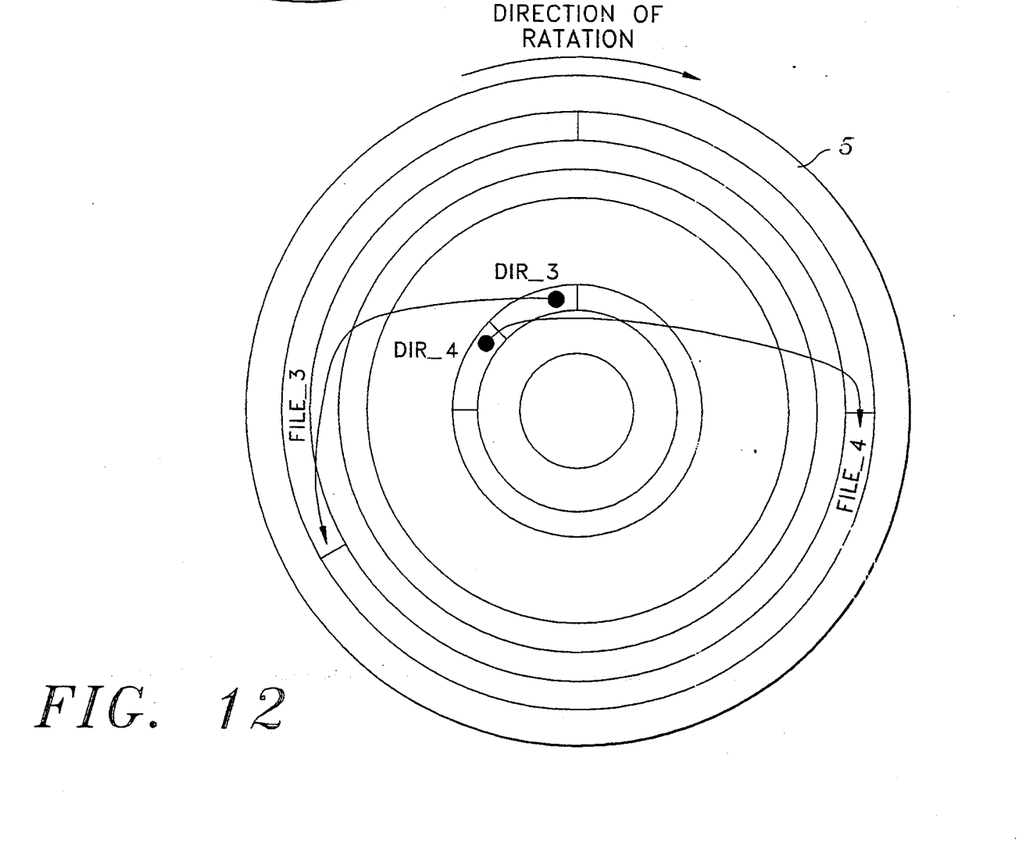

FIG. 12 shows an example of the format in which data are stored on the optical disk 5. The direction of rotation of the optical disk 5 is indicated by the arrow. When the optical disk 5 is inserted into an optical disk drive 4, access starts from a first direction, namely, the innermost part, or track of the disk 5. Data is read out in a continuous stream by moving an optical head of the drive 4 in a straight line toward the outer edge of the disk. The direction of rotation of the disk 5 is fixed and cannot be reversed. Therefore, in order to access the data in a continuous fashion, the data is stored in a continuous, contiguous stream that starts at the inner part of the disk and goes toward the outer edge. The speed of the optical disk drive is usually lower than the speed at which the data are processed, so it has to be performed efficiently.

The file directory information is recorded on the optical disk 5 starting from the inner part of the disk. The substance of the file (data, etc.) is stored in a direction going towards the outer edge or track, namely, a second direction of the disk. The mechanical movements that the optical head needs to make are reduced by storing the substance of the file in contiguous sectors.

The directory has less data than the file and the speed of operation of the disk drive 4 is constant. There is thus a correlation between the directory information contained closer to the center of the disk 5 and occupying less space of the disk 5, and the file data closer to the outer perimeter and occupying more space of the disk. Thus, for the same degree of disk rotation, the appropriate directory and file data is obtained. Also, the spacing on the disk 5 allocated to directory data and file data is efficiently distributed and maximized. By having the directories use space in an outward direction and the file use space in an inward direction, effectively all the space on the disk 5 is used.

In an exemplary fashion assume two files, FILE_3 and FILE_4 are stored on the optical disk. Each file, namely, FILE_3 and FILE_4 consists of directory information and the substance of the file. When the optical disk 5 is inserted into the optical disk drive 4 the computer system 1 reads the directory information of all the files on the optical disk 5 and keeps this information in its internal memory. When a file on the optical disk 5 is accessed, for example, FILE_3 or FILE_4, only the substance of the file is accessed based on the directory information that was read into memory. This enables mechanical movements of the optical disk drive 4 to be reduced. It increases the speed and efficiency of disk access of subsequent files, for instance, from FILE_5 onwards, when large quantities of data have been stored on the optical disk 5.

The directory information includes the file name, header sector number, size, date, and so forth. When data are read from the file, FILE_3, on the optical disk 5, a search is run on the directory information that has already been read in the memory of the computer system 1 to obtain directory information relating to FILE_3. Using the header sector number for read-out and information relating to the size of the file, a command is issued instructing the optical disk drive 4 to read out the data. The data thus read out are written to memory for processing operations, such as conversion, display, and storage on a magnetic disk of the external storage 2. FILE_4 can be accessed using the same procedure.

In the described embodiment each section, namely format conversion, is configured totally or partially in software, firmware or hardware.

The optical disk storage formats are made the same. Thus by employing translation software A, B or C, or circuitry, it is possible to configure an optical disk file system that can be used on any system. Widespread implementation of this translation software A, B or C or circuitry makes it possible for a person to use the same optical disk file system anywhere.

Although this embodiment has been described with reference to optical disks, it is to be understood that the invention is not so limited. The same effect can also be obtained, for instance, by implementing the file system on removable semiconductor files, magnetic disks, digital tape or magnetic cards.

The system of the invention permits for the efficient processing of voluminous data such as radiological medical information on transportable storage media such as small optical disks. The disks can be a write once, read many memory (WORM) disks or disks capable of multiple writings. The disks can be capable of data storage on one or both sides.

In the medical field of application, it is possible with the invented system for a patient to have individual storage of their medical records, and for this to be transported from one computer based processing center to another. In the radiological field, this should minimize the misplacing and loss of images from radiologic examinations and the like which is unfortunately becoming an increasing problem in most hospitals. As the optical disc can be readable irrespective of the operating system of various different computers, the invention markedly extends the ability and accessibility and usefulness of the stored information.

Moreover, although the examples of the invention have been directed to medical type applications, it will be apparent that many other applications exist.

Many other forms of the invention exist each different from the other in matters of detail only. The scope of the invention is to be determined by the following claims.

We claim:

1. An information processing system comprising:
   an information processor having a specific one operating system selected from multiple operating systems for processing information;
   an external storage for the information processor;
   an external storage drive reactive with the information processor for storing information in the form of data and directories in a first format based on the specific one operating system on the external storage and for reading out the data and the directories in the first format from the external storage;
   an optical disk;
   an optical disk drive reactive with the information processor for storing data and directories in an independent format different from the first format and essentially independent of the multiple operating systems on the optical disk and for reading out the data and the directories in the independent format from the optical disk; and
   a format converter reactive with the optical disk drive, the external storage drive and the information processor for converting between the data and the directories in the first format supplied to and from the information processor and stored in the external storage and the data and the directories in the independent format supplied to and from the optical disk, the format converter operatingly designating an area on the external storage for storing the data and the directories in the first format and separate areas on the optical disk for storing the data and the directories separately in the independent format;
   the format converter including a first storage effecting means for effecting recordal of the directories sequentially on the optical disk starting from an inner track outwardly and for effecting recordal of the data sequentially on the optical disk starting from an outer track inwardly, and a second storage effecting means for effecting recordal of the data and the directories read out from the optical disk by the optical disk drive in one area of the external storage in a continuous form.

2. A portable optical disk for transporting information and for operation in an information processing system according to claim 1, wherein the information having been written onto the optical disk by the information processing system such that the information is readable by the information processing system including data and directories in the second format, the directories are recorded sequentially on the optical disk starting from a first track and the data is recorded sequentially on the optical disk starting from a different track.

3. A disk according to claim 2 wherein the data and the directories are each stored in a continuous form in one area.

4. A disk according to claim 2 wherein the information is medical data.

5. A disk according to claim 2 wherein the first track is an inner track and the different track is an outer track.

6. The system according to claim 1 wherein the format converter includes designation means for designating an area on the external storage for storing the data and the directories in the first format and separate areas on the optical disk for storing the data and the directories in the second format.

7. In an information processing system according to claim 1, wherein the optical disk is a portable optical disk.

8. An information processing system comprising:
   an information processor for processing information, which is operational on a one operating system selected from multiple operating systems;
   an external storage reactive with the information processor for operatively storing therein and reading therefrom data and directories in a first format based on the selected one operating system;
   an optical disk drive for storing data and directories in an independent format different from and essentially independent of any formats based on the multiple operating systems in an optical disk; and a format converter reactive with the optical disk drive, the external storage and the information processor for converting the data and directories in the first format to the data and directories in the independent format and vice versa, the format converter including designation means for designating an area on the external storage to which and from which data and directories in the first format are recordable and readable and separate areas on the optical disk to which and from which data and directories in the independent format are recordable and readable, sequential storage means for effecting recordal of the directories in the independent format sequentially on the optical disk starting from an inner track areas designated by the designation means outwardly and for effecting recordal of the data in the independent format sequentially on the optical disk starting from an outer track areas designated by the designation means inwardly and, means for effecting recordal of the data and directories in the first format obtained by conversion by the format converter from the data and directories in the independent format read out from the optical disk by the optical disk drive in one area of the external storage designated by the designation means in a continuous form whereby the optical disk is operational with an information processing system operational with the multiple operating systems compatibly.

9. A computer system comprising:

at least a first information processing system and a second information processing system; and an optical disk;

the first information processing system including:

a first information processor for processing information on a first specific operating system selected from multiple operating systems;

a first storage means reactive with the first information processor for operatively storing therein and reading therefrom data and directories in a first format based on the first specific operating system;

a first optical disk drive reactive with the first information processor and the optical disk for operatingly storing data and directories in an independent format which is specified specifically to said optical disk and which is different from and essentially independent of the multiple operating systems on the optical disk and for operatingly reading out the data and directories in the independent format from the optical disk; and a first format converter reactive with the first optical disk drive, and the first information processor for operatingly converting the data and directories in the first format to the data and directories in the independent format for storage on the optical disk and for operatingly converting data and directories read out from the optical disk in the independent format into data and directories in the first format for processing by the first information processor; and the second information processor system including:

a second information processor for processing information on a second specific operating system different from the first specific operating system and selected from the multiple operating systems;

a second storage means reactive with the second information processor for operatively storing therein and reading therefrom data and directories in a second format based on the second specific operating system;

a second optical disk drive reactive with the second information processor and the optical disk for operatingly storing data and directories in the independent format on the optical disk and for operatingly reading out the data and the directories in the independent format from the optical disk; and a second format converter reactive with the second optical disk drive, and the second information processor for operatingly converting the data and directories in the second format to the data and directories in the independent format for storage on the optical disk and for operatingly converting data and directories read out from the optical disk in the independent format into data and directories in the second format for processing by the second information processor;

whereby the optical disk is compatibly operational with the first and second information processing systems;

and wherein the conversion by the first and second format converters is effected with respective designation means for converting the format of data and directories stored in the respective first storage means, second storage means and the optical disk, and the format conversion is based upon areas designated by the designation means.

10. In a system according to claim 9, wherein the optical disk is a portable optical disk having thereon a signal information stored in the second format by using the first optical disk drive in a first information processing system, and the thus stored signal information on the portable optical disk is read out from the portable optical disk by using the second optical disk drive in the second information processing system whereby transporting the signal information between the first and the second information processing systems.

11. An information processing system comprising:

an information processor for processing information, the processor having a specific one operating system selected from multiple operating systems;

an external storage reactive with the information processor, having data and directories written therein and read therefrom in a first format based on the specific one operating system;

an optical disk drive for storing the data and the directories in an independent format different from the first format and essentially independent of the multiple operating systems on an optical disk;

a format converter reactive with the optical disk drive, the external storage and the information processor for converting between the data and the directories in the first format and the data and the directories in the independent format, the format converter including designation means for designating an area on the external storage for storing the data and the directories in the first format and separate areas on the optical disk for storing the data and the directories in the independent format;

the designation means including sequential storage means for effecting recordal of the directories sequentially on the optical disk starting from an inner track outwardly and for effecting recordal of the data sequentially on the optical disk starting from an outer track inwardly; and the designation means including means for effecting recordal of the data and the directories read out from the optical disk by the optical disk drive in one area of the external storage in a continuous form whereby the optical disk is operational with the multiple operating systems.

12. An information processing system comprising:

an information processor for processing information on a selected one of multiple operating systems;

a first storage reactive with the information processor and having data and directories stored therein and read therefrom in a first format based on the selected one operating system;

an optical disk drive reactive with an optical disk for storing and reading the data and directories in and from said optical disk in a second format which is different from the first format and which is specified specifically to said optical disk and is essentially independent of the multiple operating systems; and a format converter reactive with the optical disk drive, the first storage and the information processor and including:

designation means for designating an area on the first storage for storing the data and directories in the first format and areas on the optical disk for storing the data and directories in the second format, and the format converter operatingly converting the data and directories in the first format to the data and directories in the second format for storage by the optical disk drive in the areas of the optical disk designated by the designation means and converting the data and directories in the second format read from the optical disk by the optical disk drive to the data and directories in the first format for processing by the information processor, the format conversion being based upon the areas designated by the designation means, whereby the optical disk is operational with the multiple operating systems compatibly.

13. The system according to claim 12 wherein the designation means includes sequential storage means for effecting recordal of the directories sequentially on the optical disk starting from an inner track outwardly and for effecting recordal of the data sequentially on the optical disk starting from an outer track inwardly.

14. The system according to claim 12 wherein the format converter includes means for dividing a unit of data read out from the first storage into a plurality of data to be stored in sector portions of the optical disk.

15. The system according to claim 12, wherein the designation means operatingly designates one area of the first storage in which the data and directories read out from the optical disk by the optical disk drive are stored in a continuous form in the first format.

16. The system according to claim 12 wherein the format converter includes means for combining the data and the directories separately read from the optical disk in the second format by the optical disk drive to the data in the first format.

17. The system according to claim 12 wherein information processed is medical data.

18. The system according to claim 12 wherein the information processor is based on an operating system from the group of the PC/AT (Trademark), Macintosh (Trademark) or Sun (Trademark) systems.

19. An information processing system comprising:

an information processor for processing information on a selected one of multiple operating systems;

an external storage reactive with the information processor and having data stored therein and read therefrom in a first format based on the selected one operating system;

an optical disk drive reactive with the information processor for operatingly storing and reading data in and from an optical disk in an independent format different from the first format and essentially independent of formats based on the multiple operating systems; and a format converter reactive with the external storage, the information processor and the optical disk drive for converting the data in the first format read out from the external storage to the data in the independent format which are recordable on the optical disk by the optical disk drive and for converting the data in the independent format read out from the optical disk to the data in the first format which are recordable on the external storage, the format converter including designation means such that format conversion between different formats is based upon areas designated by the designation means whereby the optical disk is operational with different information processing systems each having an information processor based on a different one of the multiple operating systems compatibly.

20. The system according to claim 19 wherein information processed is medical data.

21. The system according to claim 19 wherein the information processor is based on an operating system from the group of the PC/AT (Trademark), Macintosh (Trademark) or Sun (Trademark) system.

22. An information processing system comprising:

an information processor for processing information on a specific one of multiple operating systems;

storing and reading means reactive with the information processor for storing and reading data and directories in an independent format essentially independent of any formats based on the multiple operating systems in and from a compatible storage:

a format converter reactive with the storing and reading means and the information processor for converting data and directories in the independent format to data and directories in a first format based on the specific one operating system and vice versa, the format converter including designation means such that conversion between different formats is based upon areas designated by the designation means; and a first storage reactive with the information processor and the format converter, for operatively storing therein and reading therefrom the data and directories in the first format, wherein said data and directories in the first format from the first storage are converted by the format converter to the data and directories in the independent format for supply to the storing and reading means, wherein the data and directories in the independent format from the storing and reading means are converted by the format converter to the data and directories in the first format which are recordable in the first storage, and wherein the storing and reading of the data and directories are effected by the information processor.

23. The system as claimed in claim 22 wherein the compatible storage is an optical disk and the storing and reading means is an optical disk drive for the optical disk.

24. An information processing system comprising:
an information processor for processing information on a selected one of multiple operating systems;
a storage reactive with the information processor and having data and directories stored therein and read therefrom in a first format based on the selected one operating system;
a format converter reactive with the storage and the information processor for converting the data and directories in the first format stored in and read out from the storage into data and directories in an independent format which is different from and independent of the formats based on the multiple operating systems; and
storing means reactive with the information processor and the format converter for operatingly storing the data and directories in the independent format in a compatible storage,
the storing means including designation means for designating areas on the compatible storage in which the data and directories in the independent format are to be stored, and sequential storage means for separately storing the data and directories in the independent format sequentially in the areas of the compatible storage designated by the designation means, the format conversion being based upon areas designated by the designation means whereby the compatible storage is operational with the multiple operating systems compatibly.

25. The system as claimed in claim 24 wherein the compatible storage is an optical disk and the storing means is an optical disk drive for the optical disk and wherein the sequential storage means operatingly stores in the optical disk the directories in the independent format sequentially in a first direction, and the data in the independent format sequentially in a second direction different from the first direction.

26. The system according to claim 24 wherein the format converter includes means for converting the data and directories separately read from the areas of the compatible storage in the independent format to the data and directories in the first format.

* * * * *

UNITED STATES PATENT AND TRADEMARK OFFICE
CERTIFICATE OF CORRECTION

PATENT NO. : 5,410,676
DATED : April 25, 1995
INVENTOR(S) : Huang, et al.

It is certified that error appears in the above-indentified patent and that said Letters Patent is hereby corrected as shown below:

In the Drawings, Sheet 3 of 7, in FIG. 6, delete "Directory Are 68" and insert --Directory Area 68-- therefor; Sheet 6 of 7, in FIG. 10, delete "Header Section Number 102" and insert --Header Sector Number 102-- therefor; Sheet 7 of 7, in FIG. 12, delete "Direction of Ratation" and insert --Direction of Rotation-- therefor.

Column 1, lines 26 and 27, delete "and 3.5-inch optical disks (OD). International Standards Organization which conform to "ISO" SC 23." and insert --and 3.5-inch optical disks (OD) which conform to International Standards Organization "ISO" SC23.-- therefor; line 43, delete "Angels" and insert --Angeles-- therefor.

Column 3, line 22, delete the second "have"; line 38, delete semicolon ";" after the period "."; line 50, delete semicolon ";" and insert a period --.-- therefor.

Column 4, line 45, delete "stored" and insert --storage-- therefor.

Column 6, line 31, delete "Signature,:" and insert --Signature*:-- therefor; line 40, delete "File Name,:" and insert --File Name*:-- therefor; line 45, delete "File Type,:" and insert --File Type*:-- therefor; line 47, delete "Study Type,:" and insert --Study Type*:-- therefor.

Signed and Sealed this

Fifteenth Day of August, 1995

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,410,676
DATED : April 25, 1995
INVENTOR(S) : Huang, et al.

It is certified that error appears in the above-indentified patent and that said Letters Patent is hereby corrected as shown below:

ON THE TITLE PAGE

In section [73] of the above-identified patent, please add as co-assignee --Hitachi Maxell, Ltd., Ibaraki-shi, Osaka, Japan--.

Signed and Sealed this

Tenth Day of October, 1995

*Attest:*

BRUCE LEHMAN

*Attesting Officer*     *Commissioner of Patents and Trademarks*